United States Patent
Lucas

(12) 
(10) Patent No.: US 6,402,008 B1
(45) Date of Patent: Jun. 11, 2002

(54) SURGICAL STAPLER ASSEMBLY WITH INTERCHANGEABLE HEADS

(76) Inventor: Deborah A. Lucas, 5623 Dairybrook Cove, Sugar Land, TX (US) 77479

( * ) Notice: Subject to any disclaimer, the term of this patent is extended or adjusted under 35 U.S.C. 154(b) by 0 days.

(21) Appl. No.: 09/553,906

(22) Filed: Apr. 20, 2000

Related U.S. Application Data

(60) Provisional application No. 60/129,908, filed on Apr. 19, 1999.

(51) Int. Cl.$^7$ ............................................. A61B 17/068
(52) U.S. Cl. ............................... 227/175.1; 227/176.1; 227/178.1; 227/19
(58) Field of Search ........................... 227/175.1, 176.1, 227/178.1, 180.1, 19; 606/219

(56) References Cited

U.S. PATENT DOCUMENTS

| | | | |
|---|---|---|---|
| 4,671,445 A | * | 6/1987 | Barker et al. .................. 227/19 |
| 5,651,491 A | * | 7/1997 | Heaton et al. ............ 227/176.1 |
| 6,032,849 A | * | 3/2000 | Mastri et al. ............. 227/178.1 |
| 6,102,271 A | * | 8/2000 | Longo et al. ............. 227/180.1 |

\* cited by examiner

*Primary Examiner*—Scott A. Smith
(74) *Attorney, Agent, or Firm*—Daniel N. Lundeen; Lundeen & Arismendi, LLP

(57) ABSTRACT

A surgical stapler assembly for joining a tubular prosthesis to an organic duct such as a blood vessel or artery is disclosed. The assembly has a handle and a set of interchangeable heads attachable to a distal end of the handle. Each head has a staple holder housing a plurality of radially arrayed staples, a plurality of anvils disposed concentrically opposite said staples and an annular gap between the staples and the anvils for receiving the prosthesis and an end of the organic duct. The annular gap of each head in the set has a different median diameter for use with prostheses and organic ducts of different diameters. Hammers are provided to eject the staples through the prosthesis and organic duct in the annular gap and onto the anvils. The heads can be replaceably attachable to the distal end of the handle. The annular gap can be enlarged to facilitate insertion and removal of the organic duct into and from the annular gap prior to and following ejection of the staples. The interchangeable heads can come with a pre-mounted tubular prosthesis having an inside diameter approximating an inside diameter of the annular gap.

9 Claims, 7 Drawing Sheets

SURGICAL STAPLER ASSEMBLY WITH INTERCHANGEABLE HEADS

This application claims benefit of Provisional Appln. 60/129,908 filed Apr. 19, 1999.

FIELD OF THE INVENTION

The invention relates to surgical stapler assemblies, and more particularly to surgical stapler assemblies with interchangeable heads for connecting tubular prostheses of different sizes with an organic duct such as a blood vessel or artery of a similar size.

BACKGROUND OF THE INVENTION

In the repair of the aorta with a tubular graft prosthesis, surgeons often wrap the end of the sectioned descending aorta with a length of PTFE felt and suture the felt to the aorta to form a cuff. The graft prosthesis is then sutured to the felt cuff to complete the procedure. Quite often, valuable time is lost attempting to suture the felt cuff onto the end of the aorta which is sometimes friable, and will not adequately hold the suture. In turn, this lengthens the time that the aorta is damped shut.

It would be desirable to have available an assembly which would rapidly attach the felt cuff to the end of the aorta so that the procedure can be done quickly and efficiently.

U.S. Pat. No. 5,346,115 to Perouse et al. discloses a surgical staple inserter for joining two ducts such as a blood vessel and a blood prosthesis. The staple inserter ejects staples in a radial direction relative to the axis of the ducts. In one embodiment, the patent discloses a staple holder surrounded by the prosthesis and containing a series of staples arranged in at least one ring. All the staples are ejected simultaneously. The staple inserter also includes an anvil outside the organic duct and a device for spacing apart the anvil and the staple holder in relation to their relative working positions. The points of the staples project from the staple inserter and hold the prosthesis in place during the insertion of the staple holder into the ducts.

One drawback of the device in Perouse et al. is that a complete assembly of the staple inserter is required for different sizes of aorta. The size of the aorta can vary from 12 to 14 mm on the small end to 24 to 26 mm on the large end. Unfortunately, the surgical staple inserter of Perouse et al. is designed for one size only.

Other U.S. Patents of interest include U.S. Pat. No. 5,855,312 to Toledano; U.S. Pat. No. 5,810,240 to Robertson; U.S. Pat. No. 5,732,872 to Bolduc et al.; U.S. Pat. No. 5,720,755 to Dakov; U.S. Pat. No. 5,292,053 to Bilotti et al.; and U.S. Pat. No. 5,188,638 to Tzakis.

SUMMARY OF THE INVENTION

The present invention uses a set of heads sized to accommodate various organic duct sizes which are interchangeably positioned on the end of the handle. The plurality of heads allows each head to be used with a single handle. Thus, by stocking a set or sets of the replaceable heads, only a small inventory of the handles is required. With just a single handle, a variety of sizes of heads are available to be used to accommodate the correct size of the patient's organic duct.

The present invention provides a surgical stapler assembly for joining a tubular prosthesis to an organic duct such as a blood vessel or artery. The surgical stapler assembly includes a handle and a set of interchangeable heads attachable to a distal end of the handle. Each head comprises a staple holder which includes a plurality of radially arranged staples, an anvil disposed concentrically opposite the staples, and an annular gap between the staples and the anvil for receiving the prosthesis and the end of the organic duct. The annular gap of each head in the set has a different median diameter for use with prostheses and organic ducts of different diameters. A plurality of hammers can be provided for ejecting the staples through the prosthesis and organic duct in the annular gap and oto the anvils.

The heads are preferably replaceably attachable to the distal end of the handle. The annular gap is preferably enlargable to facilitate insertion and removal of the organic duct into and from the annular gap, prior to and following ejection of the staples. Each of the interchangeable heads is preferably premounted with a tubular prosthesis having an inside diameter approximating an inside diameter of the annular gap. The handle can indude a proximal end operable for controlling ejection of the staples. Each head can include an inner tubular member housing the staples and an outer member carrying the anvil. The inner and outer members are preferably secured together at a proximal end of the annular gap.

DETAILED DESCRIPTION OF THE INVENTION

Figures 1, 2:
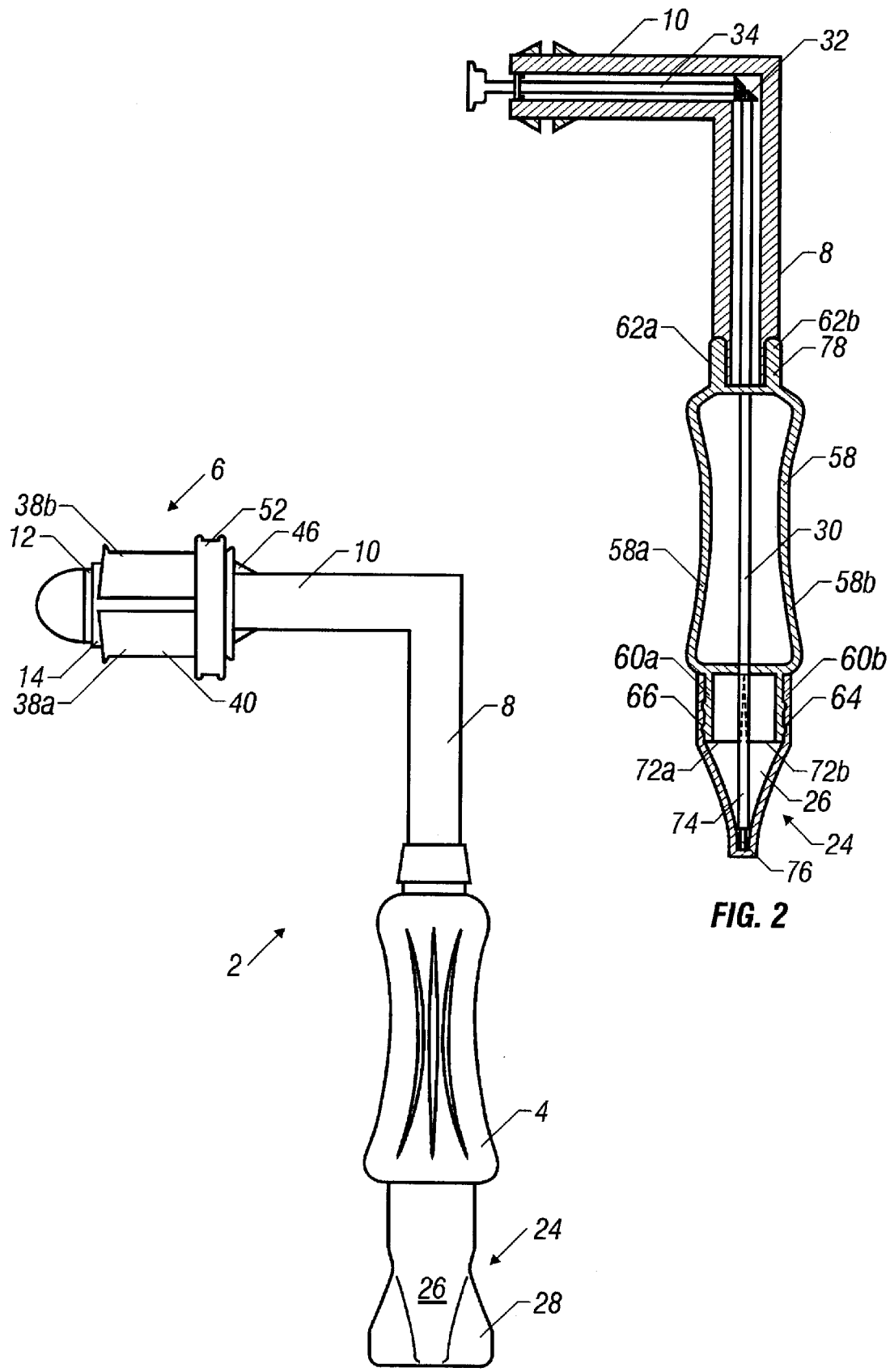
FIG. 1 is a perspective view of the surgical stapler assembly of the present invention prior to engagement with the end of an organic duct such as a descending aorta.
FIG. 2 is a longitudinal section of a handle used in the surgical stapler assembly of the present invention.
Figure 4:
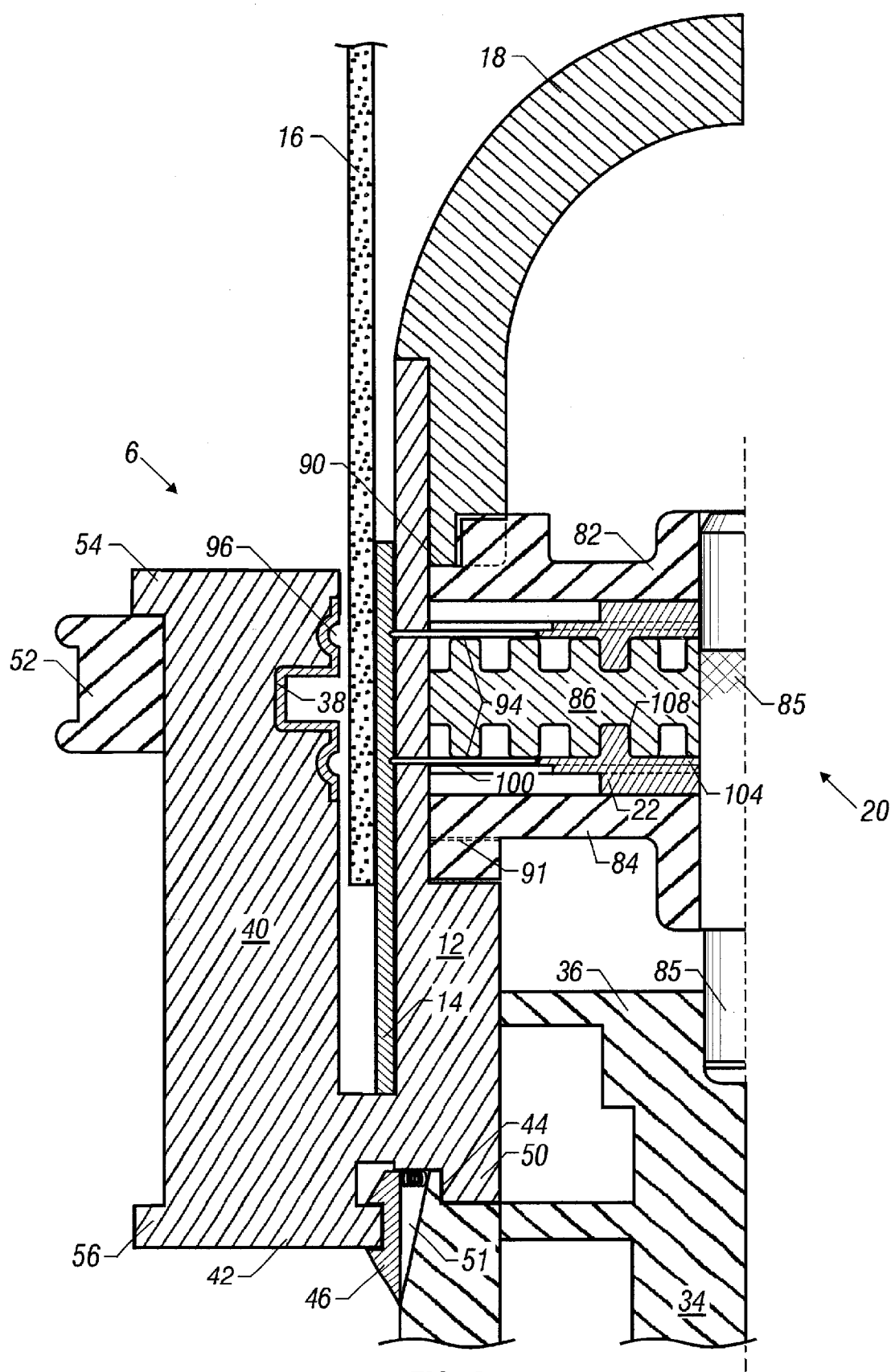
FIG. 4 is a partial longitudinal section of the head of the surgical stapler assembly attached to the handle and receiving the end of an organic duct just prior to ejection of the staples.

With reference to FIGS. 1–2 a preferred form of the surgical stapler assembly 2 includes a handle 4 and head 6. The handle 4 can be of a generally elongate form, and preferably to facilitate working in confined spaces, has an elongated proximal tube section 8 and a distal tube section 10 which is angled, more preferably at a right angle, with respect to the proximal tube section 8. The head 6 includes a tube 12 which carries a cuff 14 for insertion into an organic duct 16 (see FIGS. 4–5). The cuff 14 is placed over the external surface of the tube 12 in order to be stapled to the organic duct 16 for example a blood vessel or artery, partially covering the cuff 14 at a median region of the tube 12. The distal end of the tube 12 includes a cap 18 in the shape of a nose cone facilitating penetration of the distal end of the head 6 into the organic duct 16. The cap 18 and the part of the tube 12 around which the cuff 14 and organic duct 16 are placed constitute a part which is internal with respect to cuff 14 and organic duct 16. The rest of the head 6 constitutes a part which is external with respect to the cuff 14 and organic duct 16.

A staple holder 20 of cylindrical general shape is arranged at a median section of the tube 12. It includes hammers 22 for ejecting staples radially. The hammers 22 are controlled by the surgeon by means of a stapling wing nut 24, mounted so as to rotate on the proximal end of the handle 4. The wing nut 24 includes a cap 26 fitted with two operating fins 28 and is connected to the hammers 22 in the staple holder 20 by a linkage comprising a rod 30 connected to the staple holder 20 by a beveled gear 32, a rod 34 and a drive nut 36.

Figure 3:
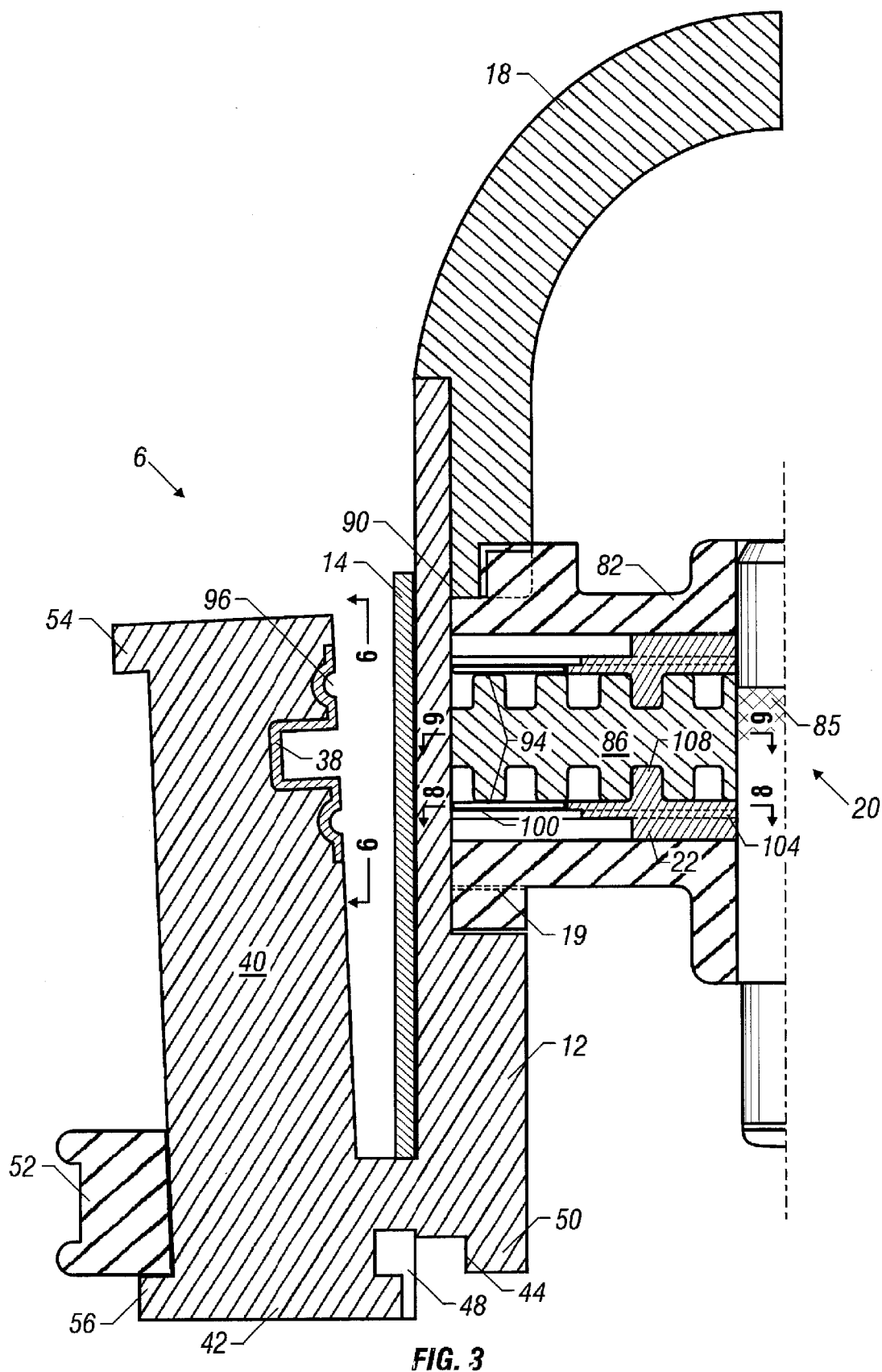
FIG. 3 is a partial longitudinal section of one embodiment of an interchangeable head used in the surgical stapler assembly of the present invention.

An anvil 38 is disposed outside the tube 36, at the staple holder 20, in order to deform the points of the staples which are ejected radially from the staple holder 20. The anvil 38 is shown in more detail in FIGS. 3 and 6 according to one embodiment. The anvil 38 consists of two anvil segments 38a, 38b, each carried by a support arm 40 of generally semi-cylindrical shape, joined to a heel 42, forming a collar connected to the tube 12. The heel 42 is secured to the tube 12 at a proximal end thereof. A shoulder 44 is formed between the heel 42 and the tube 12 for receiving the distal end of distal section 10 in interlocking engagement. A plurality of spring-biased keepers 46 (see FIGS. 2 and 4–5) mounted on the distal end of tube 10 are received in corresponding slots 48 to connect the head 6 to the handle 4. Keys 50 formed on the distal end of the tube 12 can also be provided to be received in a corresponding slot in the proximal end of the distal section 10 to further inhibit rotation of the head 6 with respect to the handle 4. To release the head 6 from the handle 4, if this is desired, the proximal ends of keepers 46 are depressed to position the distal end of the keepers 46 in a respective recess 51.

The support arms 40 are made, for example, of a relatively elastic metallic material in order to be able to space apart, approximately radially, distal ends carrying the anvil sectors 38a, 38b. Such spacing facilitates the placing of the cuff 14 and of the organic duct 16 over the tube 12, between the latter and the support arms 40.

A locking hoop 52 allows the sectors of the anvil to be assembled together after having previously disposed the organic ducts to be stapled over the internal part of the staple inserter and having positioned the support arms 40 opposite the staple holder 20. The hoop 52 can be displaced axially along the external surface of the support arms 40 between the stops 54,56 at either end thereof.

To mount the hoop 52 on support arms 40, the support arms 40 are first mounted on the tube 12 and assembled together at their heels 42. The hoop 52 is then placed around the support arms 40 while compressing them sufficiently so as to dear the stop 54 through the inside diameter of the hoop 52. Alternatively, the stop 54 and/or 56 can be secured to the support arms 40 after the hoop 52 is positioned therearound.

To assemble the handle 4, the two half-handle pieces 58a, 58b are extended at their ends on the one hand by half-sleeves 60a, 60b for supporting the wing nut 24, and on the other hand by half-sleeves 62a, 62b for fixing onto the outer tube of proximal section 8. The two half-sleeves 60a, 60b of the handpiece 58 include two annular interact with annular channels 66 of complementary shape in the internal wall of the wing nut 24, while allowing free rotation of the wing nut 24 on the handpiece 58. The proximal end of the tube 8 which is fitted into the half-sleeves 62a, 62b of the hand-piece 58 includes an annular projection 68 for axial positioning of the handpiece 58 and which interacts with an annular groove 70 of complementary shape made on the internal surfaces of the half-sleeves 62a, 62b.

In order to mount the handpiece 58, the stapling wing nut 24 is first dispersed on a support. The two half-sleeves 60a, 60b for supporting the wing nut 24 are then fitted into the cap 26 of the wing nut 24. This is done by juxtaposing joining edges 72a, 72b of the half-sleeves 60a, 60b which are symmetrically truncated, the effect of which is to form an angle between the two half-handles 58a, 58b. The proximal end 74 of the rod 30, of square cross-section, is engaged in a hole 76, of complementary shape, in the cap 26 of the wing nut 24. The proximal end of the tube 8, over which a sliding fastening hoop 78 has previously been placed, is disposed between the two half-sleeves 62a, 62b of the handpiece 58. The half-handles 58a, 58b are dosed onto each other and the fastening hoop 78 is slid over the external surfaces of the two half-sleeves 62a, 62b, wedging them together.

FIGS. 3 to 9 show an embodiment of the interchangeable head 6 which includes staple holder 20 and of the corresponding anvil 38. The staple holder 20 and the anvil 38 are disposed horizontally in FIGS. 3–5. The staple holder 20 consists of two flanges 82, 84 firmly attached to the tube 12 and carrying a rotating pin 85 onto which is fixed a disc 86 which can rotate between the flanges 82, 84. The disc 86 is pushed onto the median zone of the pin 85 which includes a portion 88 with an irregular surface ensuring better connection between the disc 86 and the pin 85. The pin 85 is adapted at one end thereof for engagement by the drive nut 36, the end of the pin 85 having an outer dimension and shape, e.g. square or hexagonal, matching the inner dimensions and shape of the drive nut 36.

The flange 82 is positioned axially inside the tube 12 between an edge 90, delimiting the opening of the cap 18, and the disc 86. The flange 84 is positioned inside the tube 12 between a shoulder 91, corresponding to an increase in the internal space of the tube 12, and the disc 86. The flanges 82, 84 are positioned transversely with respect to the tube 12 by means of axial projections 92, 93 which interact with notches 92a, 93a of complementary shape. Also, flanges 82, 84 are respectively arranged on the edge delimiting the opening of the cap 18 and on the shoulder 91 of the tube 12.

Figure 7:
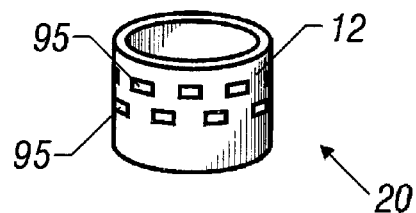
FIG. 7 is a partial perspective view of an internal part of the head of the surgical stapler assembly showing the arrangement of staple ejection orifices.
Figure 8:
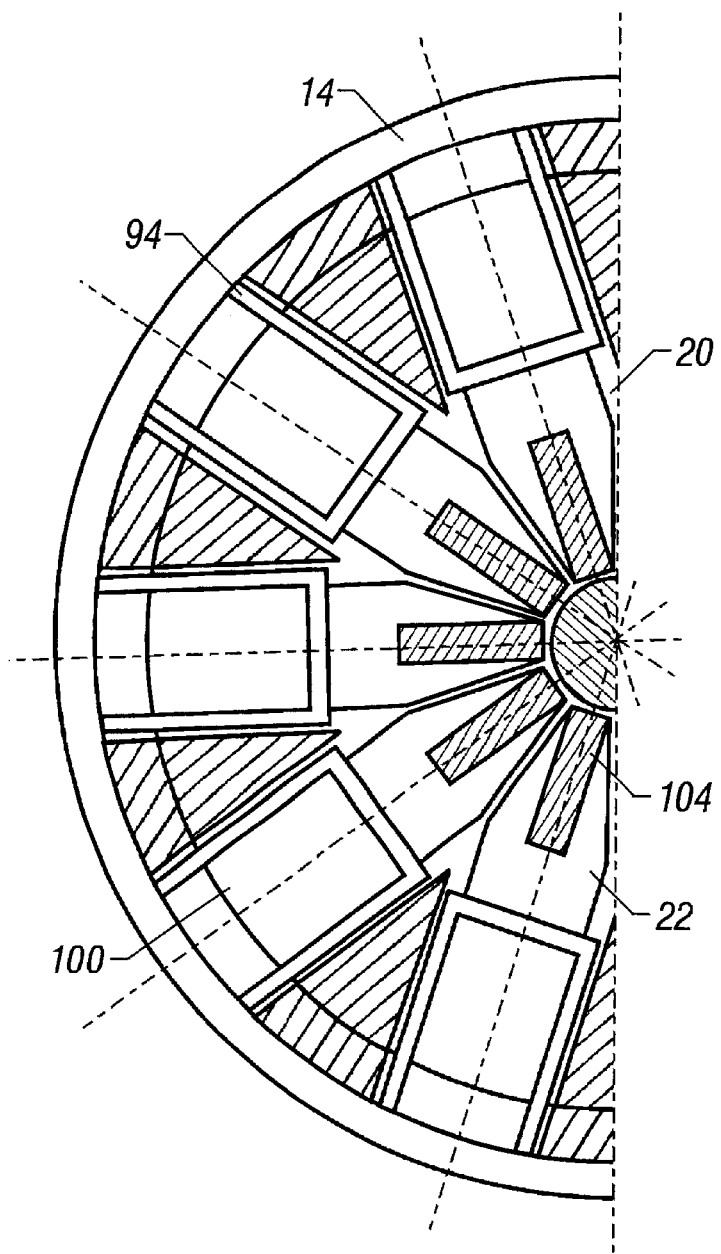
FIG. 8 is a section along the lines 8—8 in FIG. 3.

Staples 94 are disposed flat between opposite faces of the disc 86 and of flanges 82, 84, so as to constitute two superimposed rings of staples. Each ring of staples 94 includes ten staples, for example, distributed over the entire circumference of the tube 12. FIG. 7 shows how the orifices 95 of the tube 12 are arranged in two superimposed rings, so that the orifices 95 of one ring are staggered with respect to the orifices 95 of the other ring.

Figure 5:
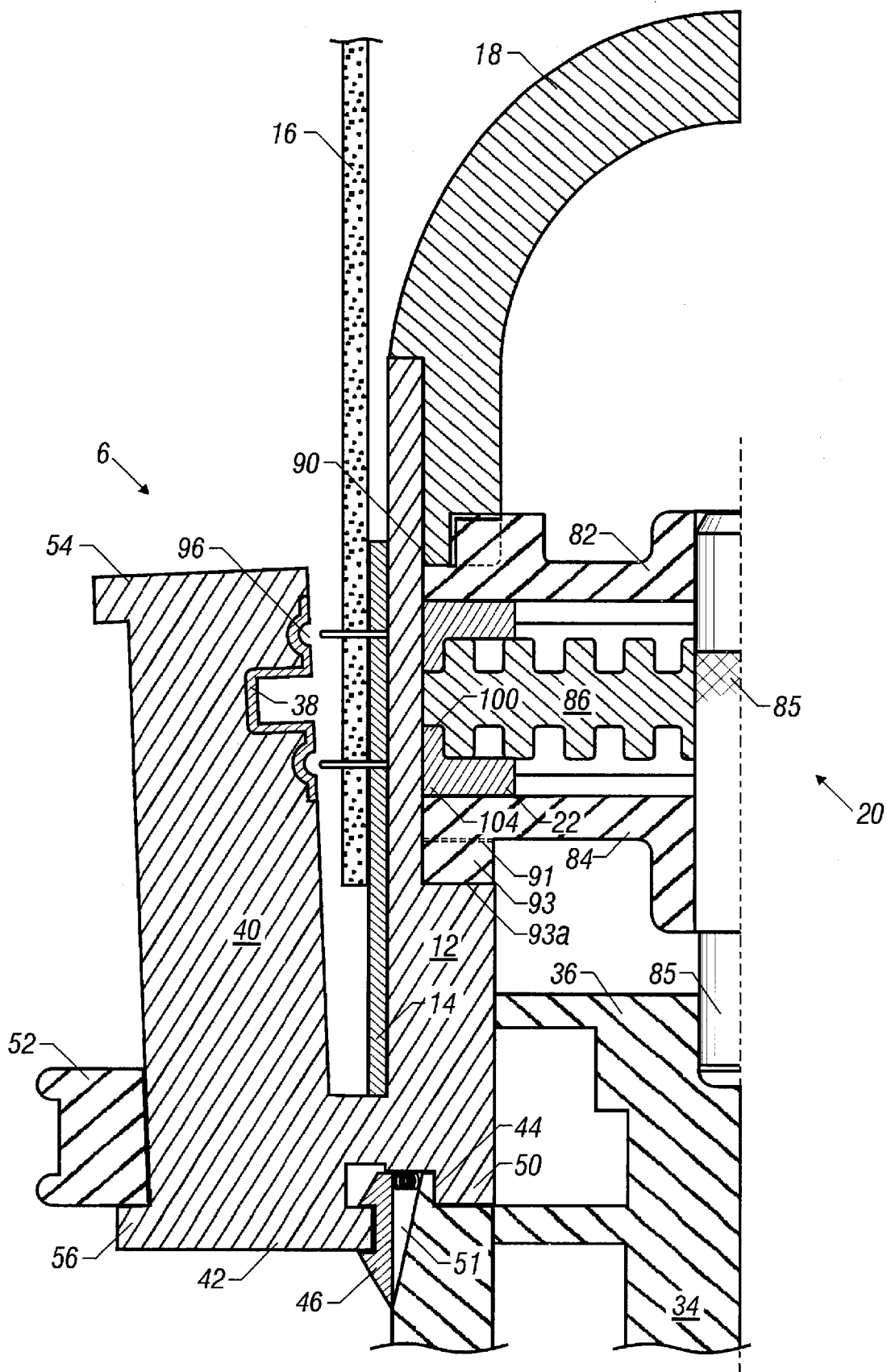
FIG. 5 is a partial longitudinal section of one embodiment of a head of the surgical stapler assembly secured to the distal end of the handle after enlarging the annular gap for release of the organic duct stapled to the tubular prosthesis.
Figure 6:
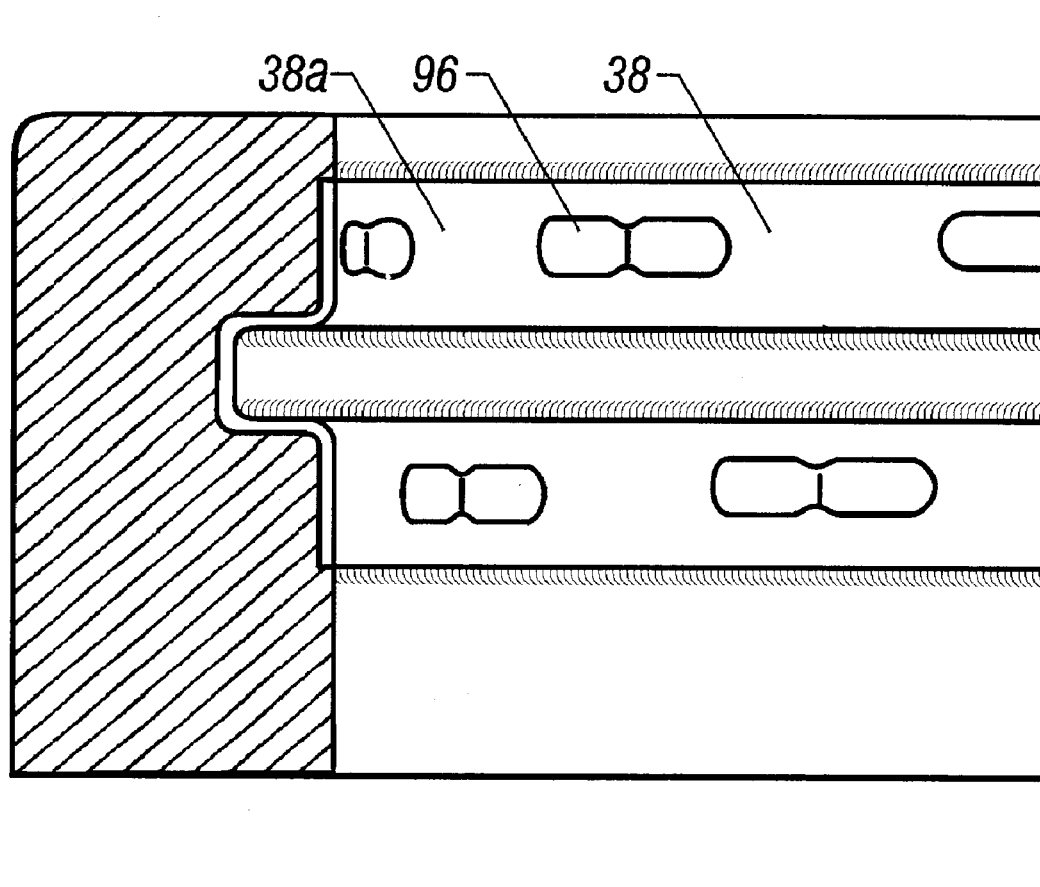
FIG. 6 is a view of half of an anvil segment along the lines 6—6 in FIG. 3.

FIG. 5 shows anvil segment 38b which includes cavities 96, of known shape, intended to receive the points of the staples in order to fold them back during stapling.

The means for ejecting the staples 94 will now be described. In this connection, reference will be made to FIGS. 3–5 and 8–9. FIGS. 3–5 and 8 show that each staple 94 is ejected by a hammer 98 of generally flat shape. The hammers 98 are disposed in rings between the opposite surfaces of the disc 86 and of flanges 82, 84. The flanges 82, 84 include, on the surfaces thereof opposite the disc 86, means for guiding the staples 94 and means for guiding the hammers 98. The means for guiding the staples 94 consist of radially extending recesses 100 in the surfaces of the flanges 82, 84, in which recesses the staples are housed. The means for guiding the hammers 98 consist of radial grooves 102 arranged on the surfaces of the flanges, in the middles of the respective recesses 100, which interact with guiding projections 104 disposed on respective faces of the hammers 98. The disc 86 includes means for driving the hammers 98, which means consist of spiral channels 106, at constant pitch, arranged symmetrically in opposite faces of the disc. The spiral channels 106 interact with respective drive projections 108 disposed on respective faces of the hammers 98.

Figure 9:
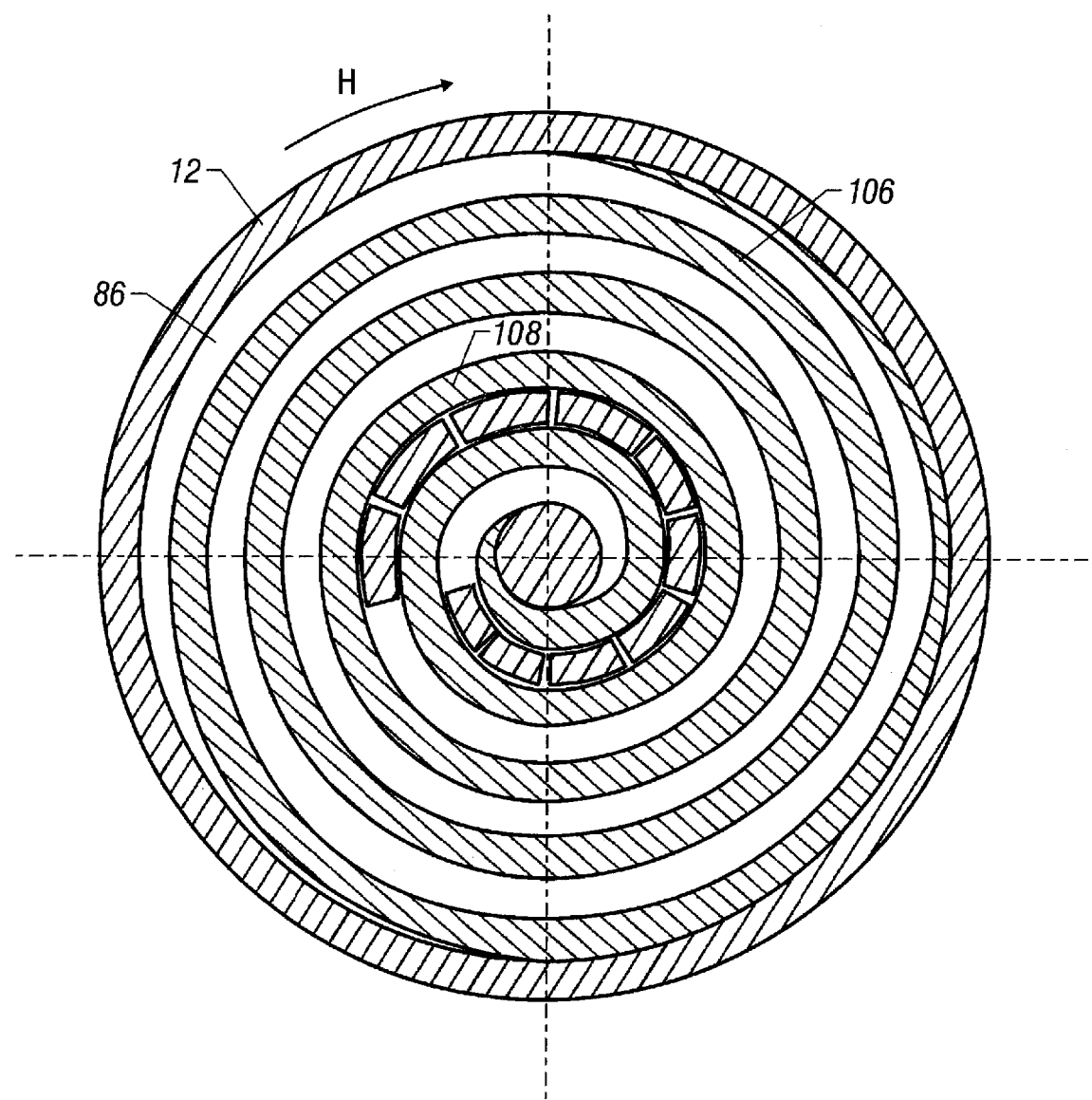
FIG. 9 is a section along the lines 9—9 in FIG. 3.

FIG. 9 shows how the projections 108 of the hammers 98 are disposed in the spiral ribs 106 of the disc 86. There are ten projections 108, corresponding to ten hammers 98, which simultaneously eject each ring of ten staples. The hammers 98 are set in their initial position, before stapling, at the center of the disc 86. The position of the projection 108 on each hammer 98 depends on the angular position of the latter in the staple holder. As the spiral channel 106 has a constant pitch, the rotation of the disc 86 in the clockwise direction, along arrow H in FIG. 9, simultaneously drives all the hammers 98, displacing them radially by an equal distance.

The mounting of the staple holder 20 according to this embodiment of the invention will now be described. In a first step, the cap 18 is placed on a support. There are then successively assembled the first flange 82, on the cap 18, the disc 86 fixed on the pin 85, and the second flange 84. The hammers 98 are next introduced into the staple holder 20. Since the position of the drive projection 108 on each hammer 98 is a function of the angular position of the latter in the staple holder 20, it is expedient to dispose the various hammers 98 in the staple holder 32 in a well-defined order. For this purpose, the first step is introducing the first hammer 98 of the series into the staple holder by engaging the drive projection 108 in the spiral channel 106, through the periphery of the disc 86, at a recess 100 for guiding the staples. The same procedure is repeated with the other hammers 98 of the series, in the order in which they are disposed in the staple holder. All the hammers 98 are set in their initial position, at the center of the disc 86, by rotating the disc 86 fully in the counterclockwise direction. The cap 28/staple holder 20 assembly is then disposed in the distal end of the tube 12. The means for axial positioning and rotational positioning of the flanges 82, 84 which were described hereinabove ensure the correspondence between the orifices 95 for ejecting the staples from the tube 12 and the recesses 100 for guiding the staples 94. The staples 94 are introduced into the staple holder 20 through the orifices 95 while orienting their points outwards and while placing the crosspiece of each staple 94 in contact with the corresponding hammer 98.

In the use of the assembly 2 to repair a damaged descending aorta, for example, the aorta is sectioned and its exposed diameter is measured. A head 6 having a tube 12/cuff 14 of a diameter about the same as the end of the aorta is selected. For this application, the set of interchangeable heads 6 are provided in 2 mm increments from 12 mm to 26 mm outside diameter. Owing to the elasticity of the aorta, it is better to use the next larger size of head 6 as the aorta can be stretched slightly. The head 6 is then attached to the handle 4, first aligning the drive nut 36 with the proximal end of the pin 85, and then the slots 48 with the keeper 46 which is snapped into place to securely connect the selected head 6 with the handle 4. With the hoop 52 positioned adjacent the proximal stop 56, the end of the aorta 16 is slid onto the cap 18 and over the tube 12 and premounted cuff 14 so as to be disposed in the annular gap between the staple holder 20 and the anvil segments 38a, 38b. The hoop 52 is then advanced in position next to the distal stop 54. Then the wing nut 24 is rotated while firmly gripping the handpiece 58 to eject the staples 94 to secure the cuff 14 to the aorta 16. The hoop 52 is then retracted in position next to the proximal stop 56 and the assembly 2 is withdrawn from the cuff 14 and aorta 16. The graft prosthesis (not shown) can then be attached to the cuff 14 by conventional suturing and or stapling. The assembly 2 can be sterilized for reuse and a new cuff 14 mounted in the interchangeable head 6, or disposed of.

What is claimed is:

1. A surgical stapler assembly for joining a tubular prosthesis to an organic duct, comprising:

a handle and a set of interchangeable heads attachable to a distal end of the handle;

each head comprising a staple holder, comprising a plurality of radially arrayed staples, an anvil disposed concentrically opposite said staples and an annular gap between said staples and said anvil for receiving the prosthesis and an end of the organic duct;

the annular gap of each head in the set having a different median diameter for use with prostheses and organic ducts of different diameters.

2. The assembly of claim 1 wherein the heads are replaceably attachable to the distal end of the handle.

3. The assembly of claim 1 comprising a plurality of hammers for ejecting the staples through the prosthesis and organic duct in the annular gap and onto the anvils.

4. The assembly of claim 3 wherein the annular gap is enlargeable to facilitate insertion and removal of the organic duct into and from the annular gap prior to and following ejection of the staples.

5. The assembly of claim 3 wherein the handle includes a proximal end operable for controlling ejection of the staples.

6. The assembly of claim 1 wherein each of the interchangeable heads is premounted with a tubular prosthesis having an inside diameter approximating an inside diameter of the annular gap.

7. The assembly of claim 1 wherein each head comprises an inner tubular member housing the staples and an outer member carrying the anvil.

8. The assembly of claim 7 wherein the inner and outer members are secured together at a proximal end of the annular gap.

9. A method for joining a tubular prosthesis to an organic duct with the surgical stapler assembly of claim 1, comprising:

determining the approximate diameter of the duct;

selecting a head having an annular gap with a median diameter approximating that of the duct;

attaching the selected head to a distal end of the handle;

receiving the prosthesis and the organic duct in the annular gap adjacent the staple holder;

ejecting the staples from the staple holder through the tubular prosthesis and organic duct and onto the anvil to staple the prosthesis and organic duct together;

disengaging the stapled tubular prosthesis and organic duct from the annular gap.

* * * * *